(12) United States Patent
Shichiri et al.

(10) Patent No.: US 9,333,194 B2
(45) Date of Patent: May 10, 2016

(54) USE OF ANSAMYCIN ANTIBIOTICS AND METHOD OF SCREENING NOVEL ANGIOGENESIS INHIBITOR

(75) Inventors: Masayoshi Shichiri, Tokyo (JP); Yujiro Tanaka, Tokyo (JP)

(73) Assignee: Japan Science & Technology Agency, Kawaguchi-shi (JP)

( * ) Notice: Subject to any disclaimer, the term of this patent is extended or adjusted under 35 U.S.C. 154(b) by 1101 days.

(21) Appl. No.: 12/504,823

(22) Filed: Jul. 17, 2009

(65) Prior Publication Data
US 2010/0004327 A1    Jan. 7, 2010

Related U.S. Application Data

(62) Division of application No. 10/518,870, filed as application No. PCT/JP03/07813 on Jun. 19, 2003, now abandoned.

(30) Foreign Application Priority Data

Jun. 21, 2002  (JP) ................................ 2002-181281
Apr. 23, 2003  (JP) ................................ 2003-118960

(51) Int. Cl.
*A61K 31/395*  (2006.01)
*A61K 31/496*  (2006.01)
*G01N 33/50*   (2006.01)

(52) U.S. Cl.
CPC ............. *A61K 31/395* (2013.01); *A61K 31/496* (2013.01); *G01N 33/5011* (2013.01)

(58) Field of Classification Search
None
See application file for complete search history.

(56) References Cited

U.S. PATENT DOCUMENTS

| | | | |
|---|---|---|---|
| 5,202,352 A * | 4/1993 | Okada et al. | 514/475 |
| 5,306,715 A * | 4/1994 | Occelli et al. | 514/183 |
| 6,406,880 B1 * | 6/2002 | Thornton | 435/32 |

FOREIGN PATENT DOCUMENTS

WO    WO 99/58126    11/1999
WO    WO 01/11086    2/2001

OTHER PUBLICATIONS

Rifampin. National Library of Medicine—Medical Subject Headings (2007).*

(Continued)

*Primary Examiner* — Anna Pagonakis
(74) *Attorney, Agent, or Firm* — Locke Lord LLP; Peter J. Fallon (57) ABSTRACT

The present invention provides novel angiogenesis inhibitors effective, safe and highly practical for inhibition of angiogenesis in various diseases, and a method for screening the same. The active ingredients of the angiogenesis inhibitors of the present invention comprise ansamycin antibiotics such as rifampicin, rifamycin SV and 3-formyl rifamycin, which have long been used extensively as antibacterial agents for treating tuberculosis or Gram-positive bacterial infections. The active ingredients of the present invention have excellent angiogenesis-inhibiting activity. The angiogenesis inhibitor of the present invention is effective for inhibition of angiogenesis in malignant tumors, diabetic retinopathy, retinal angiogenesis, inflammatory diseases, and angiogenesis accompanying cardiovascular remodeling, etc., and can be used as therapeutic agents against each disease, etc. Further, the screening method of the present invention makes it possible to perform an effective screening of angiogenesis-inhibiting substances by detecting angiogenesis-inhibiting signals based on gene expression levels.

12 Claims, 6 Drawing Sheets

(56) References Cited

OTHER PUBLICATIONS

Buffington et al. Interaction of rifampin and glucocorticoids: Adverse Effect on Renal Allograft Function. JAMA, Oct. 25, 1976, vol. 236, No. 17.*

Zetter. Angiogenesis and tumor metastasis. Annu. Rev. Med. 1998, 49: 407-24.*

Demkow et al (Pneumonologia I Alergologia Polska, 1998, Translation provided).*

MAdhusudan et al. Drug inhibition of angiogenesis. Current Opinion in Pharmacology, 2002, 2: 403-414.*

Rifampicin. DrugBank, 2008.

"Principles of Cancer Therapy." Cecil's Textbook of Medicine (Twenty-First Edition, vol. 1). W.B. Saunders Company, 2000, pp. 1060-1074.

Urszula Demkow, et aI., "The Influence of Rifampicin on Selected Parameters of Immunological Response", *Pneumonologia i Alergologia Polska*, 1998, vol. 66, No. 1-2 p. 45-53.

Demkow et al. Effect of rifampicin on selected parameters of immunological response, English language translation, 1998.

Malkowska-Zwierz, "Anti-Angiogenic Effects of Some Anti-Microbial Drugs", *International Journal of Oncology*, vol. 7, 968, 1995.

Gidoh et al., "Determination Of Three Main Antileprosy Drugs and Their Main Metabolites in Serum by HighPerformance Liquid Chromatography", *Journal of Chromatography*, 223:379-392, 1981.

Ratti et al., "Quantitative Assay of Rifampicin and its Main Metabolite 25-Desacetylrifampicin in Human Plasma by Reversed-Phase High Performance Liquid Chromatography," *Journal of Chromatography*, 225:526-531, 1981.

Acocella, "Clinical Pharmacokinetics of Rifampicin", *Clinical Pharmacokinetics*, 3: 108-127, 1978.

T. Yamashita et al., "A New Activity of Herbimycin A: Inhibition of Angiogenesis", *J. Antibiotics*, 1989, vol. 42, No. 6, p. 1015-1017.

Yoshimasa Uehara, "Mechanism of Action of an Inhibitor of src Oncogene Group Tyrosine Kinases and its Effects on Cell Transformation and Growth", *Advances in Pharmacentical Sciences*, 1992, vol. p. 82-95, Fig. 5.

Masayoshi Schichiri et aI., "Antiangiogenesis Signals by Endostatin" *FASEB Journal*, 2001, vol. 15, p. 1044-1053.

* cited by examiner

USE OF ANSAMYCIN ANTIBIOTICS AND METHOD OF SCREENING NOVEL ANGIOGENESIS INHIBITOR

This application is a divisional application of U.S. patent application Ser. No. 10/518,870 filed Aug. 29, 2005, which is a National Stage entry of the PCT application No. PCT/JP2003/007813 filed Jun. 19, 2003, which claims priority benefit of Japanese Patent Application Serial No. 2002-181281 filed Jun. 21, 2002 and Japanese Patent Application Serial No. 2003-118960 filed Apr. 23, 2003, the contents of each of which are incorporated in their entireties.

TECHNICAL FIELD

The present invention relates to an angiogenesis inhibitor, and more particularly, to a novel angiogenesis inhibitor effective for inhibition of angiogenesis in malignant tumor, diabetic retinopathy, retinal angiogenesis, inflammatory diseases, cardiovascular diseases due to cardiovascular remodeling, etc., and to a method for screening angiogenesis-inhibiting substances.

BACKGROUND ART

Angiogenesis is a process in which new blood vessels are generated from existing blood vessels, and it is known that angiogenesis is closely involved in an onset and development of diseases such as malignant (solid) tumor, diabetic retinopathy, or retinal angiogenesis, inflammatory diseases (rheumatism, etc.). For example, in order for solid tumors to grow, it is necessary to secure a supply route of nutrition and oxygen and an elimination route of wastes by angiogenesis. Angiogenesis plays an important role for tumor metastasis, an issue special concern for cancer treatment, since angiogenesis secures the blood supply. As for diabetic retinopathy, angiogenesis itself is a pathological condition, and patients lose their eyesight if left untreated. Therefore, it is considered that inhibition of angiogenesis leads to prevention/treatment of diseases, and preventing/treating agents for angiogenesis are currently explored.

Since angiogenesis promotes various pathological conditions mentioned above, inhibition of angiogenesis is expected to be beneficial in prevention/treatment of such conditions. For the purpose of prevention or treatment of diseases associated with angiogenesis, studies in search for angiogenesis-inhibiting substances have been performed. As a result, many angiogenesis-inhibiting substances have been identified, and for some of them, clinical usefulness is now under investigation.

For instance, angiogenesis inhibitors such as endostatin and angiostatin were once known to be the most potent agents for tumor dormancy therapy. They were expected to serve as ideal anticancer drugs with least adverse reactions because their systemic therapy regressed solid tumors in experimental animals remarkably (*Cell*, 88, 277-285, 1997) without any acquired resistance as experimental tumors do not develop resistance to multiple cycles of therapy unlike conventional anticancer drugs (*Nature*, 390, 404-407, 4997). However, in clinical practice, synthesis of an effective dosage of these high molecular proteins to elicit antitumor effect is difficult and costly and, consequently, business circles have already abandoned clinical applications of angiostatin, whose molecular weight is about 50000.

Endostatin, with lower molecular weight (about 20000), attracted attention and its clinical applications have started in terminal malignant tumor patients in U.S.A. However, its precise mechanisms of action as well as its receptors had been unknown.

Endostatin inhibits the proliferation of endothelial cells and induces apoptosis under reduced serum culture condition (*J. Biol. Chem.*, 274, 11721-11726, 1999), but since the effect was limited, and it was difficult to ascribe the potent effect to regress primary and metastatic cancers. Tumor cells attain accelerated proliferative characteristics not only by genomic mutation and deregulated gene expression but also by vigorously secreting many growth- and angiogenesis-promoting factors in an autocrine/paracrine fashion; and further, newly generated blood vessels supply abundant blood flow. In order for endostatin to inhibit tumor angiogenesis under such circumstances as currently reported, potent intracellular signals specifically acting on endothelial cells must be induced. These mechanisms have been unknown for long time.

On the other hand, in 1957, P. Sensi et al. of Lepetit Research Laboratories in Italy separated *Streptomyces mediterranei* (later, classified into *Nocardio mediterranei*) from soil collected at the coast of the Mediterranean, and obtained rifamycin, an antibiotic showing antibacterial activity to acid-fast bacteria and Gram-positive bacteria from the culture liquid thereof. Rifamycin in the culture liquid is a mixture comprising rifamycins A, B, C, D, E, etc., and rifamycin O is an oxidized type of rifamycin B. Rifamycin B and rifamycin O are induced into rifamycin S, and rifamycin S is reduced to rifamycin SV by ascorbic acid. 3-formyl rifamycin is made by 3-formylation of rifamycin. Rifampicin is induced from a substance made by 3-formylation of rifamycin SV. Rifamycin is collectively called as ansamycin antibiotics because it has an aromatic ring system to which an aliphatic bridge called ansa ring is connected.

In addition, the above-mentioned rifampicin is an ansamycin antibiotic developed from a collaboration of Ciba-Geigy (Switzerland) and Lepetit (Italy), and is induced from a substance made by 3-formylation of rifamycin SV. In other words, rifampicin is an ansamycin semisynthetic antibiotic having a structure of 3-{[(4-methyl-1-piperazinyl)imino]methyl}rifamycin, and is a substance which has excellent antituberculosis activity and has been used widely as an antituberculous drug. Rifampicin has antibacterial activity not only to Gram-positive bacteria but also to Gram-negative bacillus, and has been used for brucellosis, chlamydia infection, and infection of Gram-positive bacteria such as staphylococcus as well as tuberculosis.

Rifampicin is synthesized by reacting 3-formyl rifamycin SV with 1-amino-4-methylpiperazine in tetrahydrofran, and many synthetic methods including industrial synthetic methods are disclosed (Japanese Patent Publication Nos. 42-26800, 47-23303, 53-39400, 57-40155, 62-41671, 62-41672, and 62-41673).

The object of the present invention is to provide a novel angiogenesis inhibitor which is safe and highly practical, more particularly, a novel angiogenesis inhibitor which is effective, safe and highly practical for inhibition of angiogenesis in various diseases such as malignant tumor, diabetic retinopathy, retinal angiogenesis and inflammatory diseases. In addition, the present invention provides a method for screening a novel angiogenesis-inhibiting substance which serves as an active ingredient of an angiogenesis inhibitor.

As a result of intensive search to attain the objective mentioned above, the present inventors have found that rifampicin, which has excellent antituberculous and antibacterial activity to both Gram-positive and negative bacteria and widely used to treat brucellosis, chlamydia infection, and staphylococcus infection as well as tuberculosis, has excellent angiogenesis-inhibiting activity. This led to the completion of the present invention. The present invention, further confirmed that ansamycin antibiotics such as rifamycin SV or 3-formyl rifamycin have angiogenesis-inhibiting activity as well.

In the present invention, the finding that ansamycin antibiotics such as rifampicin, etc., have excellent angiogenesis-inhibiting activity has its origin in the elucidation of endostatin-induced molecular signals by the present inventors. Recently, the present inventors have found a molecular mechanism involved in inhibition of angiogenesis by endostatin (*FASEB Journal* 15, 1044-1053, 2001). Administration of endostatin at concentrations showing tumor regression in experimental animals markedly inhibited various immediately early response genes and apoptosis/cell-cycle/migration-associated genes expressed in cultured vascular endothelial cells under supplementation with serum, growth factors and angiogenesis factors.

As a result of down-regulation of a variety of gene expression, endostatin causes marginal endothelial cell proliferation, but marked inhibition of endothelial cell migration. The molecular responses, which are potent and wide spectrum of gene down-regulation by endostatin, are designated as "angiogenesis-inhibiting signals" by a present inventor. By quantifying mRNA levels using real-time quantitative PCR, it becomes possible to rapidly identify substances showing potent signals similar to endostatin among many reagents, and to examine whether they exert potent inhibition of endothelial cell migration/proliferation.

Conventional process of identifying novel angiogenesis-inhibiting factors required repetition of protein purification by extracting and fractionating tumor regressive activity released by tumor themselves from a large amount of body fluid and/or supernatant of cell cultures. The entire process was time-consuming and it took long before gene cloning. Further, it was difficult to synthesize a sufficient dosage of large molecular weight angiogenesis-inhibiting factors, endostatin and angiostatin.

By the method for screening angiogenesis-inhibiting substances which detects "angiogenesis-inhibiting signals" constructed by the present inventors, it becomes possible to detect factors exerting endostatin-type signals among many substances, and to select a novel angiogenesis-inhibiting factor by examining tumor regression activity and angiogenesis-inhibiting activity. This screening method greatly reduces conventional processes, and further, allows to estimate dosages of peptides/proteins/drugs required to induce the effect comparable to that of endostatin in advance.

The method enables to find novel factors clinically applicable to a therapy targeting new blood vessel formation in tumors. Further, when angiogenesis-inhibiting signals by endostatin are confirmed to correlate with tumor regression activity, in vitro activity of many synthetic peptides and compounds efficiently screened can be utilized. A test substance can be added to the supernatant of cultured vascular endothelial cells to detect angiogenesis-inhibiting signals, and, it becomes possible to select efficiently novel angiogenesis inhibitors from many substances. Peptides/proteins with smaller molecular weight and with structures applicable easily clinically can be preferentially selected, while potential side effects may be predicted for ingredients of drugs and food at effective concentrations to induce antiangiogenesis, in advance at the stage of screening.

In the present invention using the above-mentioned screening method, ansamycin antibiotics such as rifampicin have been found to induce strong angiogenesis-inhibiting activity among many candidate substances. Since ansamycins such as rifampicin have been widely used as antibiotics, their safety is well known and method for producing and administering them have been established. Therefore, it is expected that they can be used as highly practical angiogenesis inhibitors.

DISCLOSURE OF THE INVENTION

The present invention comprises an angiogenesis inhibitor containing an ansamycin antibiotic or a pharmacologically acceptable derivative thereof as an active ingredient ("1"), the angiogenesis inhibitor according to "1", wherein the ansamycin antibiotic is rifampicin, rifamycin SV or 3-formyl rifamycin ("2"), the angiogenesis inhibitor according to "1" or "2", wherein the pharmacologically acceptable derivative is a pharmacologically acceptable salt or a hydrate thereof ("3"), the angiogenesis inhibitor according to any one of "1" to "3", wherein angiogenesis in malignant tumor is inhibited ("4"), the angiogenesis inhibitor according to any one of "1" to "3", wherein angiogenesis in diabetic retinopathy is inhibited ("5"), the angiogenesis inhibitor according to any one of "1" to "3", wherein angiogenesis in retinal angiogenesis is inhibited ("6"), the angiogenesis inhibitor according to any one of "1" to "3", wherein angiogenesis in an inflammatory disease is inhibited ("7"), and the angiogenesis inhibitor according to any one of "1" to "3", wherein angiogenesis accompanying cardiovascular remodeling is inhibited ("8").

The present invention further comprises a method for screening an angiogenesis-inhibiting substance wherein a test substance is added to cultured vascular endothelial cells, and an angiogenesis-inhibiting signal based on gene expression level is detected ("9"), the method for screening an angiogenesis-inhibiting substance according to "9", wherein the angiogenesis-inhibiting signal based on reduced gene expression level in a cultured cell line is similar to the change induced by endostatin at a concentration showing a tumor regression effect ("10"), and the method for screening an angiogenesis-inhibiting substance according to "9" or "10", wherein the angiogenesis-inhibiting signal based on reduced gene expression level in a cultured cell line consists of one or more of an immediate early response gene or a related gene thereof, a growth/cell-cycle-related gene, a cell adhesion factor, a vasoactive factor, and a vasoactive factor receptor gene expressed in a vascular endothelial cell ("11").

BEST MODE OF CARRYING OUT THE INVENTION

The present invention comprises angiogenesis inhibitors containing an ansamycin antibiotic or a pharmacologically acceptable derivative thereof as an active ingredient. There is no particular limitation as to the subject of application of the angiogenesis inhibitor of the present invention, the angiogenesis inhibitor can be used for inhibiting angiogenesis in malignant tumors, diabetic retinopathy, retinal angiogenesis and angiogenesis accompanying inflammatory diseases or cardiovascular remodeling, as an antitumor agent, a therapeutic agent for diabetic retinopathy, retinal angiogenesis, or inflammatory diseases, or a therapeutic agent for arteriosclerosis, angiopathy, etc., respectively.

The active ingredients of the present invention comprise ansamycin antibiotics such as rifampicin, rifamycin SV, 3-formyl rifamycin, etc. The active ingredients of the present invention can be appropriately converted into, for example, pharmacologically acceptable derivatives in order to increase water-solubility for the purpose of easier administration (Japanese Patent Publication No. 5-44467). As one of the pharmacologically acceptable derivatives, it is possible to convert the ingredients into the form of pharmacologically acceptable salts or hydrates thereof, which are used in formulation of medicines usually. As mentioned above, any known producing methods can be used for preparing the active ingredients of the present invention such as rifampicin.

For administration of the angiogenesis inhibitor of the present invention, appropriate administration method such as oral or parenteral administration (intravenous, intramuscular, subcutaneous administration, or instillation) can be used in accordance with subjects of administration. In case of oral administration, the active ingredients of the present invention can be formulated as a solid or liquid prescribed drug, for instance, in the form of tablets, granules, capsules, powders, troches, solutions, suspensions, or emulsions. In case of parenteral administration, the active ingredients of the present invention can be prepared as, for example, an injectable prescribed drug by using an appropriate solvent. Examples of such solvent include water, aqueous solvents (sodium chloride solution, glucose solution, etc.), water-miscible solvents (ethyl alcohol, polyethylene glycol, propylene glycol, etc.), and nonaqueous solvents (corn oil, cottonseed oil, peanut oil, sesame oil, etc.). When applying them to diseases such as diabetic retinopathy, the active ingredients of the present invention can be administered as a formulation of eyedrops.

Dosage of the active ingredients of the present invention is appropriately determined according to subjects and forms of administration, however, as an example of dosage unit for oral administration, an amount containing about 50~1000 mg of the active ingredients, preferably, about 150~500 mg of the active ingredients, is exemplified.

Rifampicin, the active ingredients of the present invention, is a medicine which have been already used for innumerable patients including tuberculosis patients, and its dosage regimen and side effect are well known. Therefore, when using the medicines of the present invention, dosage form and dosage method based on such experiences can be used.

In addition, the present invention contains a method for screening a novel angiogenesis-inhibiting substance. The method for screening a novel angiogenesis-inhibiting substance of the present invention is conducted by adding a test substance with the use of cultured vascular endothelial cells, and detecting angiogenesis-inhibiting signals based on gene expression levels. As the angiogenesis-inhibiting signals, gene expression signals observed when endostatin is administered at a concentration showing tumor regression effects can be used. Examples of the angiogenesis-inhibiting signals based on gene expression include expression of one or more genes of immediate early response genes, their related genes, growth/cell-cycle-related genes, cell adhesion factors, vasoactive factors, and vasoactive factor receptor genes expressed in vascular endothelial cells.

Specific examples of the angiogenesis-inhibiting signal genes include: c-myc, c-fos as immediate early response genes expressed in vascular endothelial cells; max, mad, mxil as their related genes; mitogen activated protein kinase-1, mitogen activated protein kinase-2 as growth/cell-cycle-related genes; integrin-αv, integrin-β3 as cell adhesion factor; endothelin-1 gene as a vasoactive factor; and ET-A, AT1, AT2, as vasoactive factor receptor genes.

The method for screening a novel angiogenesis-inhibiting substance of the present invention to detect angiogenesis-inhibiting signals can be performed by already published technique with use of vascular endothelial cells, in particular, adult human dermal microvascular endothelial cells or human retinal endothelial cells. The quantification technique of gene expression is also already known. With the use of real-time quantitative PCR methods, angiogenesis-inhibiting signals can be detected by quantifying mRNA levels.

The present invention will be described more specifically with examples, but the technical scope of the present invention is not limited to these.

EXAMPLE 1

Angiogenesis-Inhibiting Signals by Rifampicin

Figure 1:
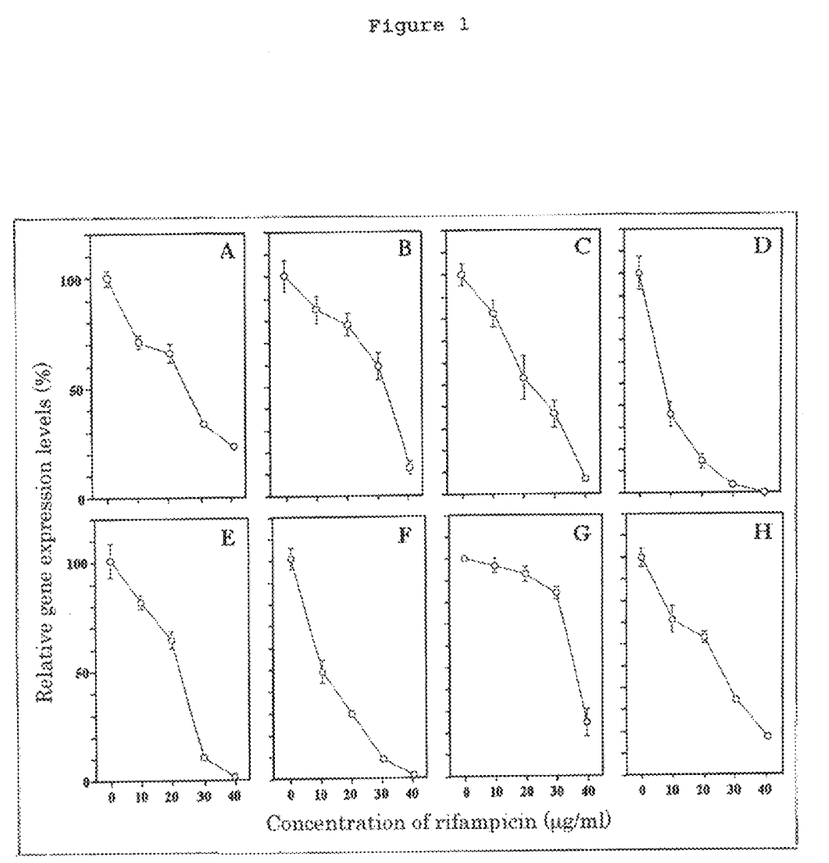
FIG. 1 is a set of views showing angiogenesis-inhibiting signals induced by addition of various concentrations of rifampicin to adult human dermal microvascular endothelial cells. A: FAK gene, B: PECAM-1 gene, C: integrin-($\alpha$v gene, D: integrin-$\beta$3 gene, E: endothelin-1 gene, F: $ET_B$ gene, G: c-myc gene, H: Flt gene.

Exponentially growing adult human dermal microvascular endothelial cells in the presence of serum/growth factors/angiogenesis-promoting factors were incubated with various concentrations of rifampicin for four hours, and extracted RNAs were subjected to quantification of mRNA of various genes using Light Cycler-based highly sensitive real-time quantitative PCR (*FASEB J.*, 15, 1044-1053, 2001). The results are shown in FIG. 1. In the figure, A represents the results of quantification of focal adhesion kinase gene, B represents those of platelet endothelial cell adhesion molecule-1 (PECAM-1) genes, C represents those of integrin-αv gene which is an adhesive factor, D represents those of integrin-β3 gene which is another adhesive factor, E represents those of endothelin-1 gene which is a vasoconstrictive peptide, F represents those of endothelin receptor subtype B ($ET_B$) gene, G represents those of c-myc gene which is an immediate early response gene, and H represents those of Flt gene which is a subtype of vascular endothelial growth factor (VEGF) receptor, respectively.

As shown in FIG. 1, addition of various concentrations of rifampicin induced angiogenesis-inhibiting signals showing spectra similar to those of endostatin.

EXAMPLE 2

Inhibitory Activity of Rifampicin Aclainst Proliferation of Vascular Endothelial Cells The effect of rifampicin on the proliferation of endothelial cells was examined by modified 72-hour-proliferation assay (*Cell,* 88, 277-85, 1997).

Under the culture in growth medium containing 10% fetal bovine serum, various concentrations of rifampicin were added to exponentially growing adult human dermal microvascular endothelial cells for 48~72 hours, and the cell number was counted by an automated blood cell counter.

Figure 2:
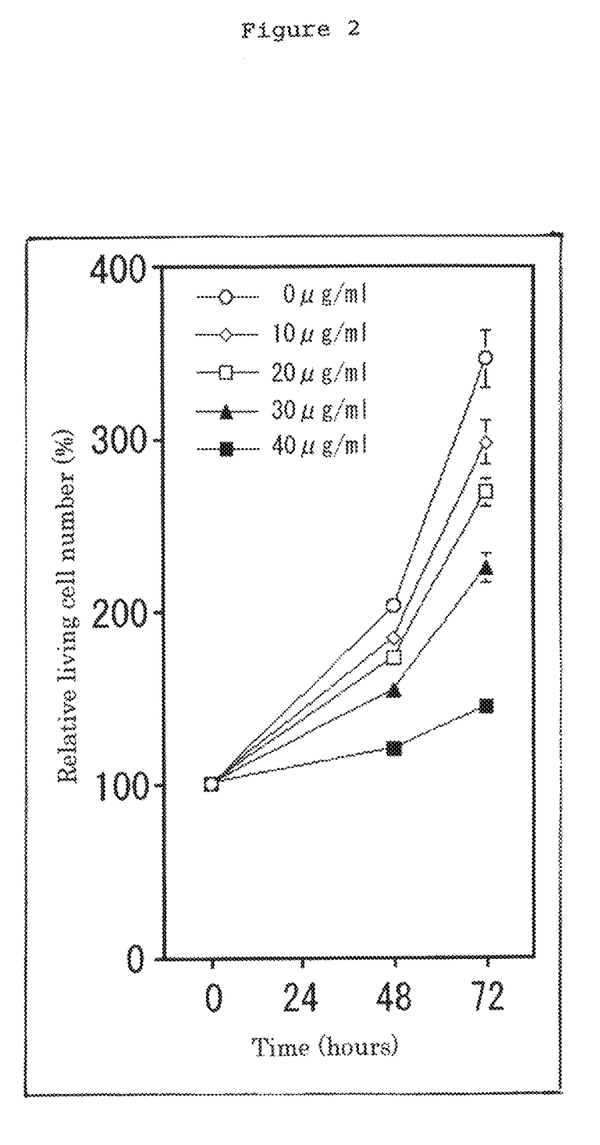
FIG. 2 is a view showing proliferation-inhibiting activity of rifampicin to adult human dermal microvascular endothelial cells with the use of modified 72-hour-proliferation assay (under the culture in proliferation medium containing 10% fetal bovine serum).

The results are shown in FIG. 2. Rifampicin inhibited the proliferation of adult human dermal microvascular endothelial cells in a concentration-dependent manner.

EXAMPLE 3

Inhibitory Activity of Rifampicin against Miciration of Vascular Endothelial Cells Inhibitory activity of rifampicin against cell migration was examined by monolayer wounding method (*FASEB J.,* 15, 1044-1053, 2001).

Confluent culture of adult human dermal microvascular endothelial cells under the culture in growth medium containing 10% fetal bovine serum were pretreated with 40 µg/ml of rifampicin for 24 hours, denuding was conducted by the monolayer wounding method, photomicrographs were taken chronologically and advanced distances of wounding edge were measured.

Figure 3:
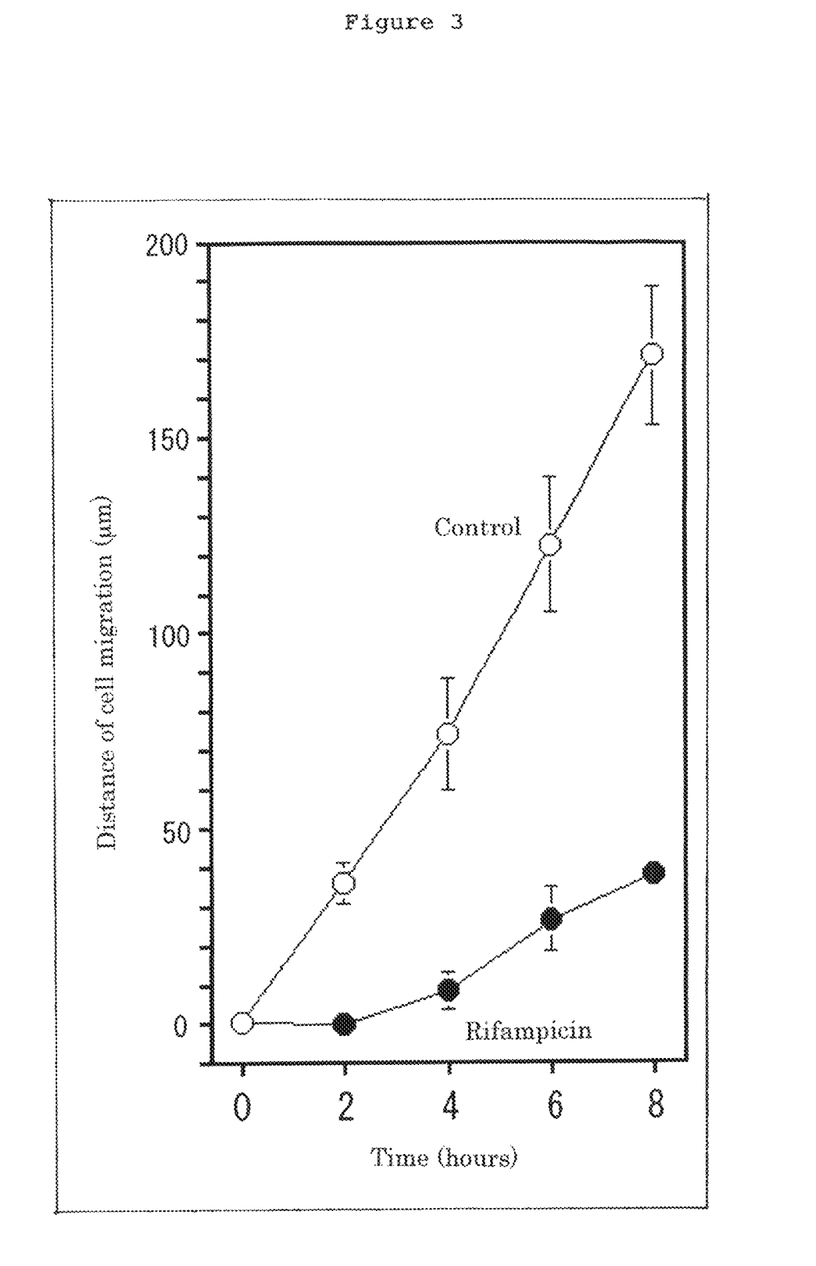
FIG. 3 is a view showing the time course of advanced distance of wounding edge after denudement of confluent culture of adult human dermal microvascular endothelial cells. Cell migration is significantly inhibited by the addition of rifampicin to the culture medium.

The results are shown in FIG. 3. The advanced distances of vascular endothelial cells were markedly decreased by the addition of 40 µg/ml of rifampicin.

As shown in FIG. 3, rifampicin inhibited chemotactic migration of adult human dermal microvascular endothelial cells.

EXAMPLE 4

Antitumor Effect in Explanted Tumors in Experimental Animals

Whether oral intake of rifampicin shows regression of primary solid tumor/metastatic tumors derived from explanted human colon cancer cell lines (CW-2) in nude mice was examined in accordance with the original method of O'Reilly et al. (*Cell,* 79, 315-28,1994; *Cell,* 88, 277-85,1997). The results are shown in FIG. 4.

Figure 4:
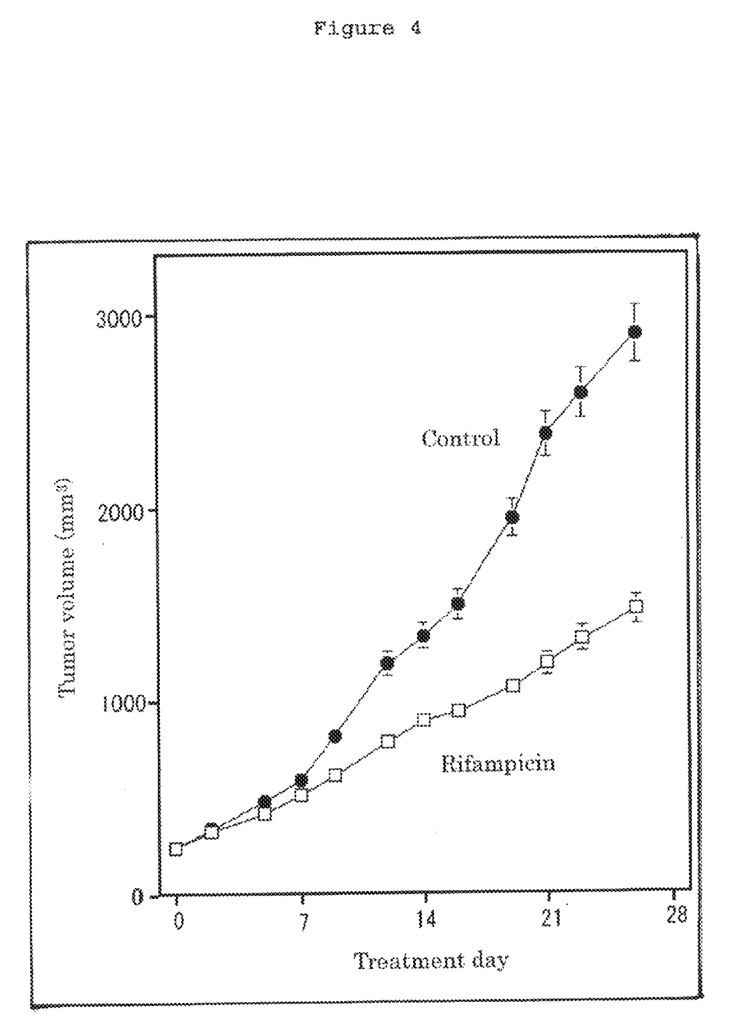
FIG. 4 is a view showing the result of examination whether oral intake of rifampicin exhibits tumor growth-inhibiting activity to explanted solid tumors derived from human colon cancer cell line (CW-2) in nude mice. Tumor volume is significantly inhibited by oral intake of rifampicin.

As shown in FIG. 4, oral intake of rifampicin starting when the size of solid tumors reached 200 mm$^3$ significantly inhibited tumor growth in comparison with a group which did not receive rifampicin.

EXAMPLE 5

Figure 5:
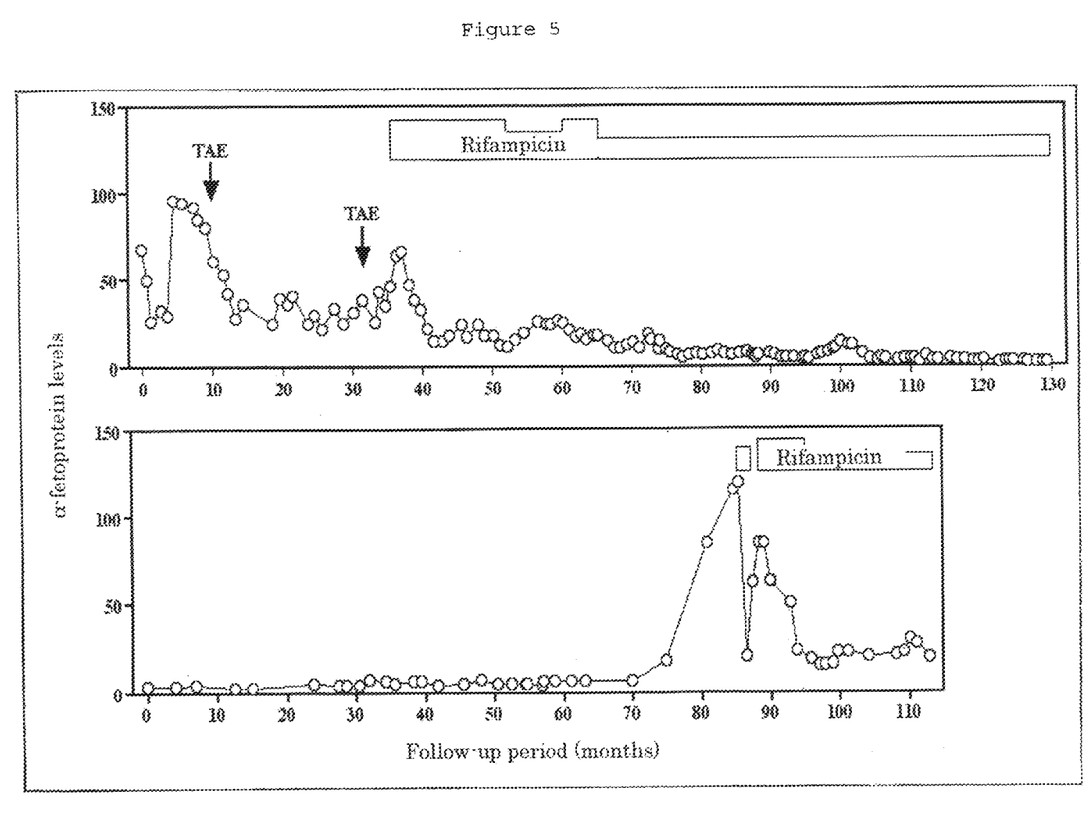
FIG. 5 is a set of views showing relationship between the changes of plasma α-fetoprotein levels and long-term rifampicin administration in two patients with hepatitis C-related liver cirrhosis combined with pulmonary tuberculosis.

Experience of Use in Patients with Hepatoma Associated with Hepatitis C-Related Liver Cirrhosis The present inventor specializing in liver diseases administered rifampicin to patients with hepatitis C-related liver cirrhosis associated with lung tuberculosis, and noted a rapid drop in plasma .alpha.-fetoprotein levels. The present inventors further noted that hepatoma never recurred during the long term despite the repeated previous episodes of recurrence. Relationship between the changes of plasma .alpha.-fetoprotein levels and rifampicin administration in two patients is shown in FIG. 5.

EXAMPLE 6

Figure 6:
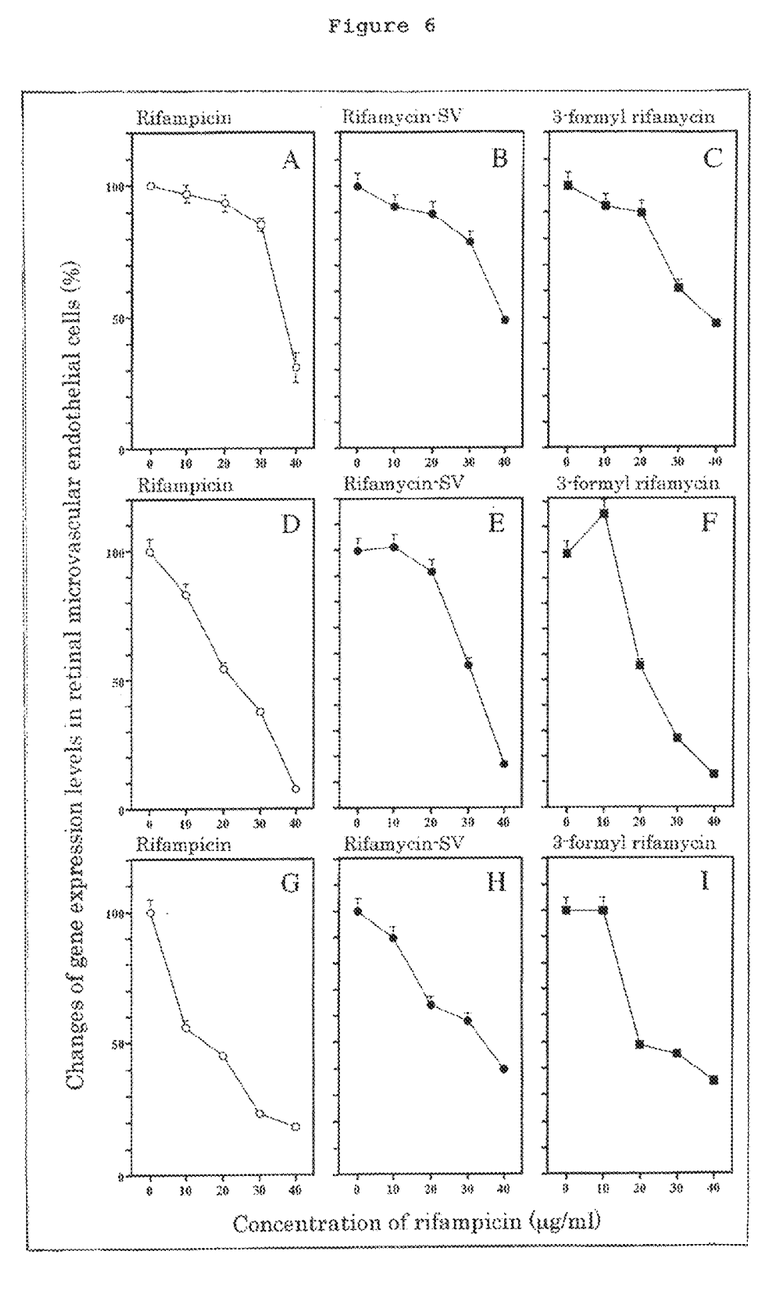
FIG. 6 is a set of views showing angiogenesis-inhibiting signals induced by various concentrations of rifampicin, rifamycin SV and 3-formyl rifamycin in human retinal microvascular endothelial cells. It is shown that each mRNA amount of c-myc, integrin-αv, integrin-β3 is inhibited in a concentration-dependent manner.

Angiogenesis-lnhibiting Signals (The Changes of Gene Expression Levels) Induced by Addition of Rifampicin, Rifamycin SV and 3-Formyl Rifamycin Human retinal microvascular endothelial cells were rendered to grow exponentially in the presence of serum/growth factors/angiogenesis-promoting factors, and various concentrations of rifampicin, rifamycin SV and 3-formyl rifamycin were added. After four hours-incubation, RNA was extracted and subjected to mRNA quantification of various genes using aforementioned LightCycler-based highly sensitive real-time quantitative PCR. The results are shown in FIG. 6. A, B and C represent the quantification results of c-myc gene; D, E and F represent those of integrin-αv gene; G, H and I represent those of integrin-β3 gene. Further, A, D and G indicate the changes of mRNA levels after adding rifampicin; B, E and H indicate those after adding rifamycin SV; C, F and I indicate those after adding 3-formyl rifamycin. As shown in FIG. 6, angiogenesis-inhibiting signals are markedly elicited by rifampicin in human retinal microvascular endothelial cells as well, which constitute diabetic retinopathy. Simultaneously, it is revealed that both rifamycin SV and 3-formyl rifamycin, derivatives of rifampicin, exhibit similar activity potently.

INDUSTRIAL APPLICABILITY

The present invention would provide angiogenesis inhibitors having potent angiogenesis-inhibiting activity and used for wide range of diseases including malignant tumor, diabetic retinopathy, retinal angiogenesis, inflammatory diseases and cardiovascular diseases, as an antitumor agent, a therapeutic agent for diabetic retinopathy, retinal angiogenesis, inflammatory diseases, or cardiovascular diseases, etc., respectively. Because rifampicin, the active ingredient of the present invention, has been used as an antibacterial medicine, its safety has been confirmed and methods for production and administration established, therefore, the angiogenesis inhibitors of the present invention are promising as highly practical angiogenesis inhibitors. The present invention also provides a method for screening a novel angiogenesis-inhibiting substance which serves as an active ingredient of angiogenesis inhibitors. The method for screening angiogenesis-inhibiting substances of the present invention which detects "angiogenesis-inhibiting signals" based on gene expression, allows to efficiently detect substances having angiogenesis-inhibiting activity among many substances whose action is unknown. This screening method greatly shortens conventional screening processes, and further, it makes it possible to estimate dosages of peptides/proteins/drugs required to express the effect comparable to that of the existing pharmaceutical, endostatin.

What is claimed is:

1. A method of inhibiting a tumor induced angiogenesis comprising administering to a malignant tumor patient an effective amount of rifampicin as an active ingredient.

2. The method according to claim 1, wherein the rifampicin is a pharmacologically acceptable salt or a hydrate thereof.

3. The method according to claim 1, wherein the rifampicin is administered orally to a malignant tumor patient.

4. The method according to claim 3, wherein the effective amount is 50-1000 mg of the active ingredient.

5. The method according to claim 3, wherein the effective amount is 150-500 mg of the active ingredient.

6. The method according to claim 1, wherein the rifampicin is administered parenterally to a malignant tumor patient.

7. A method of treating a malignant tumor comprising administering to a malignant tumor patient an effective amount of rifampicin as an active ingredient, wherein the malignant tumor is treated by inhibiting a tumor induced angiogenesis.

8. The method according to claim 7, wherein the rifampicin is a pharmacologically acceptable salt or a hydrate thereof.

9. The method according to claim 7, wherein the rifampicin is administered orally to a malignant tumor patient.

10. The method according to claim 9, wherein the effective amount is 50-1000 mg of the active ingredient.

11. The method according to claim 9, wherein the effective amount is 150-500 mg of the active ingredient.

12. The method according to claim 7, wherein the rifampicin is administered parenterally to a malignant tumor patient.

* * * * *